US008580851B2

(12) United States Patent
Ueno

(10) Patent No.: US 8,580,851 B2
(45) Date of Patent: Nov. 12, 2013

(54) OPHTHALMIC SOLUTION

(75) Inventor: Ryuji Ueno, Montgomery, MD (US)

(73) Assignee: Sucampo AG, Zug (CH)

( * ) Notice: Subject to any disclaimer, the term of this patent is extended or adjusted under 35 U.S.C. 154(b) by 399 days.

(21) Appl. No.: 11/110,698

(22) Filed: Apr. 21, 2005

(65) Prior Publication Data

US 2005/0222265 A1 Oct. 6, 2005

Related U.S. Application Data

(63) Continuation-in-part of application No. PCT/JP2004/003288, filed on Mar. 12, 2004, which is a continuation-in-part of application No. 10/644,870, filed on Aug. 21, 2003, now abandoned.

(60) Provisional application No. 60/404,779, filed on Aug. 21, 2002.

(51) Int. Cl.
*A61K 31/215* (2006.01)

(52) U.S. Cl.
USPC .......................................... 514/530; 514/912

(58) Field of Classification Search
USPC ......................................... 514/530, 912, 573
See application file for complete search history.

(56) References Cited

U.S. PATENT DOCUMENTS

| | | |
|---|---|---|
| 4,136,173 A | 1/1979 | Pramoda et al. |
| 4,136,177 A | 1/1979 | Lin et al. |
| 5,001,153 A | 3/1991 | Ueno et al. |
| 5,151,444 A | 9/1992 | Ueno et al. |
| 5,166,178 A | 11/1992 | Ueno et al. |
| 5,194,429 A | 3/1993 | Ueno et al. |
| 5,208,256 A | 5/1993 | Ueno |
| 5,212,324 A | 5/1993 | Ueno |
| 5,221,690 A | 6/1993 | Sugiyama et al. |
| 5,236,907 A | 8/1993 | Ueno et al. |
| 5,558,876 A | 9/1996 | Desai et al. |
| 5,627,208 A | 5/1997 | Stjernschantz et al. |
| 5,686,487 A | 11/1997 | Ueno |
| 5,773,471 A | 6/1998 | Oguchi et al. |
| 2002/0002185 A1 | 1/2002 | Reed et al. |
| 2002/0094981 A1 | 7/2002 | Ponticello et al. |
| 2002/0103255 A1 | 8/2002 | Hellberg et al. |

FOREIGN PATENT DOCUMENTS

| | | |
|---|---|---|
| EP | 1 224 935 A2 | 7/2002 |
| JP | 2001-81048 A | 3/2001 |
| JP | 2001-335511 A | 12/2001 |
| JP | 2002-104970 A | 4/2002 |
| JP | 2002-510654 A | 4/2002 |
| WO | 94/08585 A1 | 4/1994 |
| WO | 96/40051 A1 | 12/1996 |
| WO | 00/18316 A2 | 4/2000 |
| WO | 01/74314 A2 | 10/2001 |
| WO | 02/092098 A1 | 11/2002 |
| WO | 02/100437 A2 | 12/2002 |
| WO | 2004/112836 A2 | 12/2004 |

*Primary Examiner* — Zohreh Fay

(74) *Attorney, Agent, or Firm* — Sughrue Mion, PLLC

(57) ABSTRACT

The present invention relates to an ophthalmic solution comprising a prostaglandin compound and viscosity-increasing compound. The ophthalmic solution of the invention is excellent in stability and can provide long lasting and increased effect when administrated topically to the eyes of a patient.

9 Claims, No Drawings

OPHTHALMIC SOLUTION

CROSS REFERENCE TO RELATED APPLICATION

This application is a continuation-in-part application of U.S. Ser. No. 10/644,870 filed on Aug. 21, 2003, now abandoned claiming the benefit of 35 U.S.C. 119(e) on U.S. Provisional Application No. 60/404,779 filed on Aug. 21, 2002 and International Patent Application No. PCT/JP2004/003288 filed on Mar. 12, 2004 designating U.S.

FIELD OF THE INVENTION

The present invention relates to an ophthalmic solution or an eye drop composition comprising a prostaglandin compound and a viscosity-increasing compound.

The present invention also relates to a method for treating glaucoma and/or ocular hypertension.

BACKGROUND ART

Prostaglandins (hereinafter, referred to as PGs) are members of class of organic carboxylic acids, which are contained in tissues or organs of human and other mammals, and exhibit a wide range of physiological activities. PGs found in nature (primary PGs) have, as a general structural property thereof, a prostanoic acid skeleton as shown in the formula (A):

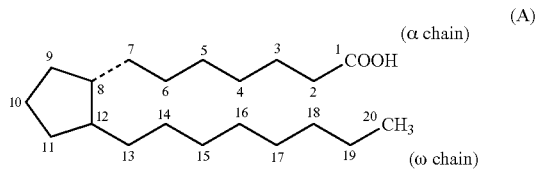 [SMILES: CCCCCCCCC1CCC[C@@H]1CCCCCCC(=O)O]

(A)

On the other hand, some synthetic analogues have modified skeletons. The primary PGs are classified into PGAs, PGBs, PGCS, PGDs, PGEs, PGFs, PGGs, PGHs, PGIs and PGJs on the basis of the structural property of the five membered ring moiety, and further classified into the following three types by the number and position of the unsaturated bond in the carbon chain moiety.
Type 1 (subscript 1): 13,14-unsaturated-15-OH
Type 2 (subscript 2): 5,6- and 13,14-diunsaturated-15-OH
Type 3 (subscript 3): 5,6-, 13,14-, and 17,18-triunsaturated-15-OH.

Further, PGFs are classified on the basis of the configuration of the hydroxyl group at the 9-position into α type (wherein the hydroxyl group is of the α-configuration) and β type (wherein the hydroxyl group is of the β-configuration).

In addition, some 15-keto-PGs (PGs having an oxo group at position 15 in place of the hydroxy group) and 13,14-dihydro-15-keto-PGs have been known as substances naturally produced by enzymatic actions during metabolism of the primary PGs. 15-keto-PGs have been disclosed in U.S. Pat. Nos. 5,073,569, 5,534,547, 5,225,439, 5,166,174, 5,428,062 5,380,709 5,886,034 6,265,440, 5,106,869, 5,221,763, 5,591,887, 5,770,759 and 5,739,161. The contents of these publications are herein incorporated by reference.

Some prostaglandin compounds have been known to be useful as pharmaceutical agents in the ophthalmic area, namely as an ocular hypotensive agent or an agent for treatment of glaucoma. For example, latanoprost, that is 13,14-dihydro-17-phenyl-18,19,20-trior-PGF$_{2\alpha}$ isopropyl ester, travoprost, that is 16-(3-trifluoromethyl phenoxy)-17,18,19,20-tetranor PGF$_{2\alpha}$ isopropyl ester and bimatoprost, that is 17-phenyl-18,19,20-trinor-PGF$_{2\alpha}$ N-ethylamide have already been placed on the market under the name of Xalatan™, Travatan™ and Lumigan™ eye drops for the treatment of glaucoma and ocular hypertension.

Further, 15-keto-prostaglandin compounds have been known to be useful as pharmaceutical agents in the ophthalmic area, namely as an ocular hypotensive agent or an agent for treatment of glaucoma, see U.S. Pat. Nos. 5,001,153; 5,151,444, 5,166,178, 5,194,429 and 5,236,907, for treatment of cataract, see U.S. Pat. Nos. 5,212,324 and 5,686,487, for increasing the choroidal blood flow, see U.S. Pat. No. 5,221,690 and for treatment of optic nerve disorders, see U.S. Pat. No. 5,773,471. The contents of these USPs are herein incorporated by reference. Especially, isopropyl ester of 13,14-dihydro-15-keto-20-ethyl-PGF2α has already been placed on the market under the name of Rescula™ (common name: isopropyl unoprostone) ophthalmic solution for treatment of glaucoma and ocular hypertension. Rescula™ ophthalmic solution provides sufficient ocular hypotensive effect by administrating twice a day.

SUMMARY OF THE INVENTION

An object of the present invention is to provide an ophthalmic solution, which is excellent in stability, potency or duration of the activity.

This inventor found that an ophthalmic solution comprising a PG compound and a specific viscosity-increasing compound is excellent in stability and provides long-lasting and increased effects and therefore, said ophthalmic solution shows great advantages.

Accordingly, the present invention provides an ophthalmic solution comprising a prostaglandin compound of formula (I) shown below and at least one viscosity-increasing compound selected from the group consisting of acrylate polymers, polyols, cellulose polymers, polysaccharides and polyl-lactams.

The present invention also provides a method for improving the duration of the effect of an ophthalmic solution comprising a prostaylandin compound of formula (I) shown below when administrated to the eyes of a subject, comprising: adding at least one viscosity-increasing compound selected from the group consisting of acrylate polymers, polyols, cellulose polymers, polysaccharides and polyl-lactams to the ophthalmic solution.

The present invention further provides a method for treating ocular hypertension and/or glaucoma, which comprises administrating an ophthalmic solution comprising as an active ingredient thereof a prostaglandin compound of formula (I) shown below and at least one viscosity-increasing compound selected from the group consisting of acrylate polymers, polyols, cellulose polymers, polysaccharides and polyl-lactams.

DETAILED DESCRIPTION

The nomenclature of the PG compounds used herein is based on the numbering system of prostanoic acid represented in the above formula (A).

The formula (A) shows a basic skeleton of the C-20 PG compound, but the present invention is not limited to those having the same number of Carbon atoms. In the formula (A), the numbering of the carbon atoms which constitute the basic skeleton of the PG compounds starts at the carboxylic acid (numbered 1), and carbon atoms in the α-chain are numbered 2 to 7 towards the five-membered ring, those in the ring are 8 to 12, and those in the ω-chain are 13 to 20. When the number of carbon atoms is decreased in the α-chain, the number is deleted in the order starting from position 2; and when the number of carbon atoms is increased in the α-chain, compounds are named as substitution compounds having respective substituents at position 2 in place of carboxy group (C-1). Similarly, when the number of carbon atoms is decreased in the ω-chain, the number is deleted in the order starting from position 20; and when the number of carbon atoms is increased in the ω-chain, compounds are named as substitution compounds having respective substituents at position 20. Stereochemistry of the compounds is the same as that of the above formula (A) unless otherwise specified.

In general, each of PGD, PGE and PGF represents a PG compound having hydroxy groups at positions 9 and/or 11, but in the present specification they also include those having substituents other than the hydroxyl groups at positions 9 and/or 11. Such compounds are referred to as 9-dehydroxy-9-substituted-PG compounds or 11-dehydroxy-11-substituted-PG compounds. A PG compound having hydrogen in place of the hydroxy group is simply named as 9- or 11-dehydroxy compound.

As stated above, the nomenclature of PG compounds is based on the prostanoic acid skeleton. However, in case the compound has a similar partial construction as a prostaglandin, the abbreviation of "PG" may be used. Thus, a PG compound of which α-chain is extended by two carbon atoms, that is, having 9 carbon atoms in the α-chain is named as 2-decarboxy-2-(2-carboxyethyl)-PG compound. Similarly, a PG compound having 11 carbon atoms in the α-chain is named as 2-decarboxy-2-(4-carboxybutyl)-PG compound. Further, a PG compound of which ω-chain is extended by two carbon atoms, that is, having 10 carbon atoms in the ω-chain is named as 20-ethyl-PG compound. These compounds, however, may also be named according to the IUPAC nomenclatures.

According to the IUPAC naming system, for example, 13,14-dihydro-15-keto-16R,S-fluoro-PGE$_2$ is (Z)-7-{(1R,2R,3R)-3-hydroxy-2-[(4R,S)-fluoro-3-oxo-1-octyl]-5-oxo-cyclopentyl}-hept-5-enoic acid; 13,14-dihydro-15-keto-20-ethyl-11-dehydroxy-11R-methyl-PGE$_2$ methyl ester is methyl 7-{(1R,2S,3S)-3-methyl-2-[3-oxo-1-decyl]-5-oxo-cyclopentyl}-hept-5-enoate; and 13,14-dihydro-6,15-diketo-19-methyl-PGE$_2$ ethyl ester is ethyl 7-{(1R,2S,3S)-3-hydroxy-2-(7-methyl-3-oxo-1-octyl)-5-oxocyclopentyl}-6-oxo-heptanoate. 13,14-dihydro-15-keto-20-ethyl-PGF$_2$α isopropyl ester is isopropyl (Z)-7-[(1R,2R,3R,5S)-3,5-dihydro-2-{3-oxo-1-decyl)-cyclopentyl]-hept-5-enoate; and 13,14-dihydro-15-keto-20-methyl-PGF$_2$α methyl ester is methyl (Z)-7-[(1R,2R,3R,5S)-3,5-dihydroxy-2-{3-oxo-1-nonyl}-cyclopentyl]-hept-5-enoate.

The 15-keto-PG compound used in the present invention may be any derivative of a PG insofar as having an oxo group at position 15 in place of the hydroxy group, and may further include a compound having one double bond between positions 13 and 14 (15-keto-PG type 1 compound), two double bonds between positions 13 and 14, and positions 5 and 6 (15-keto-PG type 2 compound), and three double bonds between positions 5 and 6, positions 13 and 14, and positions 17 and 18(15-keto-PG type 3 compound), and a derivative thereof wherein the bond between the positions 13 and 14 is single bond, in place of the double bond (13,14-dihydro-15-keto-PG compound).

Typical examples of the PG compounds used in the present invention include 15-keto-PG type 1, 15-keto-PG type 2, 15-keto-PG type 3, 13,14-dihydro-15-keto-PG type 1, 13,14-dihydro-15-keto-PG type 2, 13,14-dihydro-15-keto-PG type 3 and the derivatives thereof.

Examples of the substitution compounds or derivatives include a PG compound of which the carboxy group at the end of the alpha chain is esterified; physiologically acceptable salt thereof; an unsaturated derivative having a double bond between positions 2 and 3 or a triple bond between positions 5 and 6; PG compounds having substituent(s) on carbon atom(s) at position(s) 3, 5, 6, 16, 17, 18, 19 and/or 20; and PG compounds having lower alkyl or a hydroxy (lower) alkyl group at position 9 and/or 11 in place of the hydroxy group.

According to the present invention, preferred substituents on the carbon atom at position(s) 3, 17, 18 and/or 19 include alkyl having 1-4 carbon atoms, especially methyl and ethyl. Preferred substituents on the carbon atom at position 16 include lower alkyl such as methyl and ethyl, hydroxy, halogen atom such as chlorine and fluorine, and aryloxy such as trifluoromethylphenoxy. Preferred substituents on the carbon atom at position 17 include halogen atom such as chlorine and fluorine Preferred substituents on the carbon atom at position 20 include saturated or unsaturated lower alkyl such as $C_{1-4}$ alkyl, lower alkoxy such as $C_{1-4}$ alkoxy, and lower alkoxy alkyl such as $C_{1-4}$ alkoxy-$C_{1-4}$ alkyl. Preferred substituents on the carbon atom at position 5 include halogen atoms such as chlorine and fluorine. Preferred substituents on the carbon atom at position 6 include an oxo group forming a carbonyl group. Stereochemistry of PGs having hydroxy, lower alkyl or hydroxy(lower)alkyl substituent on the carbon atom at positions 9 and 11 may be α, β or a mixture thereof.

Further, the above described derivatives may have a ω chain shorter than that of the primary PGs and a substituent such as alkoxy, cyclohexyl, cyclohexyloxy, phenoxy and phenyl at the end of the truncated ω-chain.

Especially preferred compounds include a 13,14-dihydro-15-keto-PG compound that has a single bond between positions 13 and 14; a 15-keto-20-lower alkyl (especially ethyl) PG compound that has a lower alkyl, especially ethyl, at carbon atom of position 20; a 15-keto-PGF compound that has hydroxy groups at positions 9 and position 11 of the five memberd ring.

A preferred prostaglandin compound used in the present invention is represented by the formula (I):

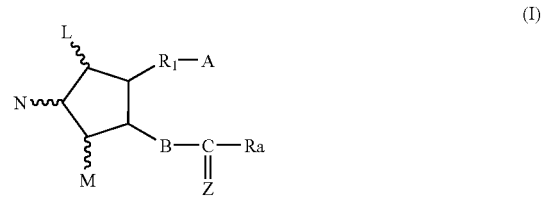

(I)

wherein L, M and N are hydrogen, hydroxy, halogen, lower alkyl, hydroxy(lower)alkyl, lower alkanoyloxy or oxo, wherein at least one of L and M is a group other than hydrogen, and the five-membered ring may have at least one double bond;

A is —CH$_3$, or —CH$_2$OH, —COCH$_2$OH, —COOH or a functional derivative thereof;

B is —CH$_2$—CH$_2$—, —CH=CH—, —C≡C—, —CH$_2$—CH$_2$—CH$_2$—, —CH=CH—CH$_2$—, —CH$_2$—CH=CH—, —C≡C—CH$_2$— or —CH$_2$—C≡C—;

Z is

wherein $R_4$ and $R_5$ are hydrogen, hydroxy, halogen, lower alkyl, lower alkoxy or hydroxy(lower)alkyl, wherein $R_4$ and $R_5$ are not hydroxy and lower alkoxy at the same time;

$R_1$ is a saturated or unsaturated bivalent lower or medium aliphatic hydrocarbon residue, which is unsubstituted or substituted with halogen, alkyl, hydroxy, oxo, aryl or heterocyclic group, and at least one carbon atom in the aliphatic hydrocarbon is optionally substituted by oxygen, nitrogen or sulfur; and Ra is a saturated or unsaturated lower or medium aliphatic hydrocarbon residue, which is unsubstituted or substituted with halogen, oxo, hydroxy, lower alkoxy, lower alkanoyloxy, cyclo(lower)alkyl, cyclo(lower)alkyloxy, aryl, aryloxy, heterocyclic group or hetrocyclic-oxy group, and at least one carbon atom in the aliphatic hydrocarbon is optionally substituted by oxygen, nitrogen or sulfur; lower alkoxy; lower alkanoyloxy; cyclo(lower)alkyl; cyclo(lower)alkyloxy; aryl; aryloxy; heterocyclic group; heterocyclic-oxy group.

A more preferred prostaglandin compound used in the present invention is represented by the formula (II):

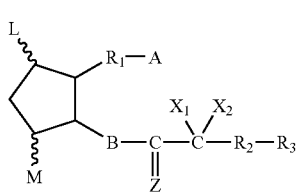

wherein L and M are hydrogen, hydroxy, halogen, lower alkyl, hydroxy(lower)alkyl, lower alkanoyloxy or oxo, wherein at least one of L and M is a group other than hydrogen, and the five-membered ring may have one or more double bonds;

A is —$CH_3$, or —$CH_2OH$, —$COCH_2OH$, —COOH or a functional derivative thereof;

B is —$CH_2$—$CH_2$—, —CH=CH—, —C≡C—, —$CH_2$—$CH_2$—$CH_2$—, —CH=CH—$CH_2$—, —$CH_2$—CH=CH—, —C≡C—$CH_2$— or —$CH_2$—C≡C—;

z is

wherein $R_4$ and $R_5$ are hydrogen, hydroxy, halogen, lower alkyl, lower alkoxy or hydroxy(lower)alkyl, wherein $R_4$ and $R_5$ are not hydroxy and lower alkoxy at the same time;

$X_1$ and $X_2$ are hydrogen, lower alkyl, or halogen;

$R_1$ is a saturated or unsaturated bivalent lower or medium aliphatic hydrocarbon residue, which is unsubstituted or substituted with halogen, alkyl, hydroxy, oxo, aryl or heterocyclic group, and at least one carbon atom in the aliphatic hydrocarbon is optionally substituted by oxygen, nitrogen or sulfur;

$R_2$ is a single bond or lower alkylene, and at least one carbon atom in the lower alkylene is optionally substituted by oxygen, nitrogen or sulfur; and $R_3$ is lower alkyl, lower alkoxy, lower alkanoyloxy, cyclo(lower) alkyl, cyclo(lower)alkyloxy, aryl, aryloxy, heterocyclic group or heterocyclic-oxy group.

In the above formula, the term "unsaturated" in the definitions for $R_1$ and Ra is intended to include at least one or more double bonds and/or triple bonds that are isolatedly, separately or serially present between carbon atoms of the main and/or side chains. According to the usual nomenclature, an unsaturated bond between two serial positions is represented by denoting the lower number of the two positions, and an unsaturated bond between two distal positions is represented by denoting both of the positions.

The term "lower or medium aliphatic hydrocarbon" refers to a straight or branched chain hydrocarbon group having 1 to 14 carbon atoms (for a side chain, 1 to 3 carbon atoms are preferable) and preferably 1 to 10, especially 1 to 8 carbon atoms.

The term "halogen atom" covers fluorine, chlorine, bromine and iodine.

The term "lower" throughout the specification is intended to include a group having 1 to 6 carbon atoms unless otherwise specified.

The term "lower alkyl" refers to a straight or branched chain saturated hydrocarbon group containing 1 to 6 carbon atoms and includes, for example, methyl, ethyl, propyl, isopropyl, butyl, isobutyl, t-butyl, pentyl and hexyl.

The term "lower alkylene" refers to a straight or branched chain bivalent saturated hydrocarbon group containing 1 to 6 carbon atoms and includes, for example, methylene, ethylene, propylene, isopropylene, butylene, isobutylene, t-butylene, pentylene and hexylene.

The term "lower alkoxy" refers to a group of lower alkyl-O—, wherein lower alkyl is as defined above.

The term "hydroxy(lower)alkyl" refers to a lower alkyl as defined above which is substituted with at least one hydroxy group such as hydroxymethyl, 1-hydroxyethyl, 2-hydroxyethyl and 1-methyl-1-hydroxyethyl.

The term "lower alkanoyloxy" refers to a group represented by the formula RCO—O—, wherein RCO— is an acyl group formed by oxidation of a lower alkyl group as defined above, such as acetyl.

The term "cyclo(lower)alkyl" refers to a cyclic group formed by cyclization of a lower alkyl group as defined above but contains three or more carbon atoms, and includes, for example, cyclopropyl, cyclobutyl, cyclopentyl and cyclohexyl.

The term "cyclo(lower)alkyloxy" refers to the group of cyclo(lower)alkyl-O—, wherein cyclo(lower)alkyl is as defined above.

The term "aryl" may include unsubstituted or substituted aromatic hydrocarbon rings (preferably monocyclic groups), for example, phenyl, tolyl, xylyl. Examples of the substituents are halogen atom and halo(lower)alkyl, wherein halogen atom and lower alkyl are as defined above.

The term "aryloxy" refers to a group represented by the formula ArO—, wherein Ar is aryl as defined above.

The term "heterocyclic group" may include mono- to tricyclic, preferably monocyclic heterocyclic group which is 5 to 14, preferably 5 to 10 membered ring having optionally substituted carbon atom and 1 to 4, preferably 1 to 3 of 1 or 2 type of hetero atoms selected from nitrogen atom, oxygen atom and sulfur atom. Examples of the heterocyclic group include furyl, thienyl, pyrrolyl, oxazolyl, isoxazolyl, thiazolyl, isothiazolyl, imidazolyl, pyrazolyl, furazanyl, pyranyl, pyridyl, pyridazinyl, pyrimidyl, pyrazinyl, 2-pyrrolinyl, pyrrolidinyl, 2-imidazolinyl, imidazolidinyl, 2-pyrazolinyl, pyrazolidinyl, piperidino, piperazinyl, morpholino, indolyl, benzothienyl, quinolyl, isoquinolyl, purinyl, quinazolinyl, carbazolyl, acridinyl, phenanthridinyl, benzimidazolyl, benzimidazolinyl, benzothiazolyl, phenothiazinyl. Examples of the substituent in this case include halogen, and halogen substituted lower alkyl group, wherein halogen atom and lower alkyl group are as described above.

The term "heterocyclic-oxy group" means a group represented by the formula HcO-, wherein Hc is a heterocyclic group as described above.

The term "functional derivative" of A includes salts, preferably pharmaceutically acceptable salts, ethers, esters and amides.

Suitable "pharmaceutically acceptable salts" include salts formed with non-toxic bases conventionally used in pharmaceutical field, for example a salt with an inorganic base such as an alkali metal salt (such as sodium salt and potassium salt), an alkaline earth metal salt (such as calcium salt and magnesium salt), an ammonium salt; or a salt with an organic base, for example, an amine salt including such as methylamine salt, dimethylamine salt, cyclohexylamine salt, benzylamine salt, piperidine salt, ethylenediamine salt, ethanolamine salt, diethanolamine salt, triethanolamine salt, tris (hydroxymethylamino) ethane salt, monomethyl-monoethanolamine salt, procaine salt and caffeine salt), a basic amino acid salt (such as arginine salt and lysine salt), tetraalkyl ammonium salt and the like. These salts may be prepared by a conventional process, for example from the corresponding acid and base or by salt interchange.

Examples of the ethers include alkyl ethers, for example, lower alkyl ethers such as methyl ether, ethyl ether, propyl ether, isopropyl ether, butyl ether, isobutyl ether, t-butyl ether, pentyl ether and 1-cyclopropyl ethyl ether; and medium or higher alkyl ethers such as octyl ether, diethylhexyl ether, lauryl ether and cetyl ether; unsaturated ethers such as oleyl ether and linolenyl ether; lower alkenyl ethers such as vinyl ether, allyl ether; lower alkynyl ethers such as ethynyl ether and propynyl ether; hydroxy(lower)alkyl ethers such as hydroxyethyl ether and hydroxyisopropyl ether; lower alkoxy (lower)alkyl ethers such as methoxymethyl ether and 1-methoxyethyl ether; optionally substituted aryl ethers such as phenyl ether, tosyl ether, t-butylphenyl ether, salicyl ether, 3,4-di-methoxyphenyl ether and benzamidophenyl ether; and aryl(lower)alkyl ethers such as benzyl ether, trityl ether and benzhydryl ether.

Examples of the esters include aliphatic esters, for example, lower alkyl esters such as methyl ester, ethyl ester, propyl ester, isopropyl ester, butyl ester, isobutyl ester, t-butyl ester, pentyl ester and 1-cyclopropylethyl ester; lower alkenyl esters such as vinyl ester and allyl ester; lower alkynyl esters such as ethynyl ester and propynyl ester; hydroxy(lower) alkyl ester such as hydroxyethyl ester; lower alkoxy (lower) alkyl esters such as methoxymethyl ester and 1-methoxyethyl ester; and optionally substituted aryl esters such as, for example, phenyl ester, tolyl ester, t-butylphenyl ester, salicyl ester, 3,4-di-methoxyphenyl ester and benzamidophenyl ester; and aryl(lower)alkyl ester such as benzyl ester, trityl ester and benzhydryl ester.

The amide of A means a group represented by the formula —CONR'R", wherein each of R' and R" is hydrogen, lower alkyl, aryl, alkyl- or aryl-sulfonyl, lower alkenyl and lower alkynyl, and include for example lower alkyl amides such as methylamide, ethylamide, dimethylamide and diethylamide; arylamides such as anilide and toluidide; and alkyl- or arylsulfonylamides such as methylsulfonylamide, ethylsulfonylamide and tolylsulfonylamide.

Preferred examples of L and M include hydrogen, hydroxy and oxo, and especially, a compound wherein both of L and M are hydroxy which has a 5-membered ring structure of, so called, PGF type, or a compound wherein L is hydroxy and M is oxo which has a 5-membered ring structure of, so called, PGE type. PGF type is more preferable.

Preferred example of A is —COOH, its pharmaceutically acceptable salt, ester or amide thereof.

Preferred example of B is —$CH_2$—$CH_2$—, which provides a compound so called 13,14-dihydro type PG.

Preferred examples of $X_1$ and $X_2$ comprise hydrogen and halogen and preferably, both are hydrogen atom or at least one of them is a halogen. The compound wherein both of $X_1$ and $X_2$ are fluorine, which provides a compound so called 16,16-difluoro type PG, is also preferable.

Preferred $R_1$ is a hydrocarbon residue containing 1-10 carbon atoms, preferably 6-10 carbon atoms. Further, at least one carbon atom in the aliphatic hydrocarbon is optionally substituted by oxygen, nitrogen or sulfur.

Examples of $R_1$ include, for example, the following groups:

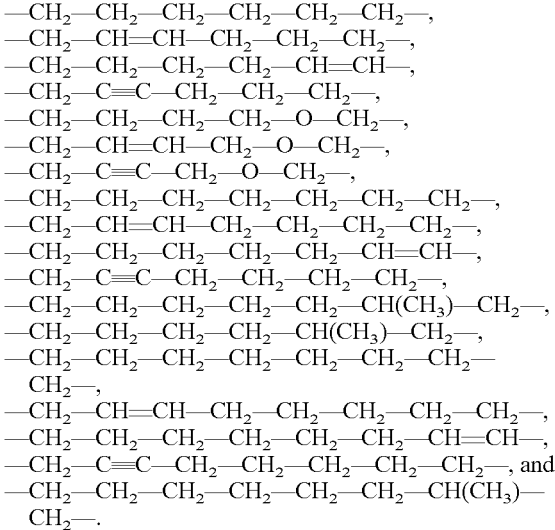

Preferred Ra is a hydrocarbon containing 1-10 carbon atoms, more preferably, 1-8 carbon atoms. Ra may have one or two side chains having one carbon atom.

The configuration of the ring and the α- and/or ω chains in the above formula (I) and (II) may be the same as or different from that of the primary PGs. However, the present invention also includes a mixture of a compound having a primary type configuration and a compound of a non-primary type configuration.

The typical example of the present compounds are 13,14-dihydro-15-keto-20-ethyl-PGF compound or 13,14-dihydro-15-keto-17-phenyl-18,19,20-trinor-prostaglandin F compound and its derivative or analogue, or 13,14-dihydro-17-phenyl-18,19,20-trior-PGF2α isopropyl ester, 16-(3-trifluoromethyl phenoxy)-17,18,19,20-tetranor $PGF_{2\alpha}$ isopropyl ester or 17-phenyl-18,19,20-trinor-$PGF_{2\alpha}$ N-ethylamide.

In the present invention, the PG compound which is dihydro between 13 and 14, and keto (=O) at 15 position may be in the keto-acetal equilibrium by formation of a hemiacetal between hydroxy at position 11 and keto at position 15.

For example, it has been revealed that when both of $X_1$ and $X_2$ are halogen atoms, especially, fluorine atoms, the compound contains a tautomeric isomer, bicyclic compound.

If such tautomeric isomers as above are present, the proportion of both tautomeric isomers varies with the structure of the rest of the molecule or the kind of the substituent present. Sometimes one isomer may predominantly be present in comparison with the other. However, it is to be appreciated that the present invention includes both isomers.

Further, the 15-keto-PG compounds used in the invention include the bicyclic compound and analogs or derivatives thereof.

The bicyclic compound is represented by the formula (III)

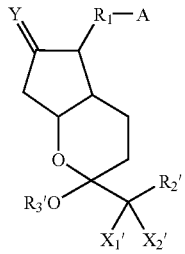

(III)

wherein, A is —$CH_3$, or —$CH_2OH$, —$COCH_2OH$, —COOH or a functional derivative thereof;

$X_1'$ and $X_2'$ are hydrogen, lower alkyl, or halogen;

Y is

wherein $R_4'$ and $R_5'$ are hydrogen, hydroxy, halogen, lower alkyl, lower alkoxy or hydroxy(lower)alkyl, wherein $R_4'$ and $R_5'$ are not hydroxy and lower alkoxy at the same time.

$R_1$ is a saturated or unsaturated bivalent lower or medium aliphatic hydrocarbon residue, which is unsubstituted or substituted with halogen, alkyl, hydroxy, oxo, aryl or heterocyclic group, and at least one carbon atom in the aliphatic hydrocarbon is optionally substituted by oxygen, nitrogen or sulfur; and $R_2'$ is a saturated or unsaturated lower or medium aliphatic hydrocarbon residue, which is unsubstituted or substituted with halogen, oxo, hydroxy, lower alkoxy, lower alkanoyloxy, cyclo(lower)alkyl, cyclo(lower)alkyloxy, aryl, aryloxy, heterocyclic group or hetrocyclic-oxy group; lower alkoxy; lower alkanoyloxy; cyclo(lower)alkyl; cyclo(lower)alkyloxy; aryl; aryloxy; heterocyclic group; heterocyclic-oxy group.

$R_3'$ is hydrogen, lower alkyl, cyclo(lower)alkyl, aryl or heterocyclic group.

Furthermore, while the compounds used in the invention may be represented by a formula or name based on keto-type regardless of the presence or absence of the isomers, it is to be noted that such structure or name does not intend to exclude the acetal type compound.

In the present invention, any of isomers such as the individual tautomeric isomers, the mixture thereof, or optical isomers, the mixture thereof, a racemic mixture, and other steric isomers may be used in the same purpose.

Some of the compounds used in the present invention may be prepared by the method disclosed in U.S. Pat. Nos. 5,073,569, 5,166,174, 5,221,763, 5,212,324, 5,739,161 and 6,242,485 these cited references are herein incorporated by reference.

The PG compounds described as above are useful as agent for treating various symptoms in the ophthalmic area. For example, it is useful for treating glaucoma and/or ocular hypertension, cataract and optic nerve disorders and for increasing the choroidal blood flow.

The term "ophthalmic solution" used herein refers any form of liquid composition suitable for topical eye administration and the liquid composition may be in the form of solution, emulsion or suspension.

The term "treatment" or "treating" used herein refers to any means of control of a condition including prevention, cure, relief of the condition, and arrestation or relief of development of the condition.

In the ophthalmic solution of the present invention, the PG compound, the active ingredient, may be any of the above described compounds.

The amount of the PG compound in the ophthalmic solution is not limited as long as it is sufficient to provide the expected therapeutic effects. In general, the amount of the PG compound in the solution may be from about 0.00001 to about 10 w/v %, preferably, about 0.0001 to about 5 w/v %, more preferably about 0.001 to about 1 w/v % of the solution.

In this specification and claims, "viscosity-increasing compound" represents a polymer compound which can increase viscosity of an aqueous medium when it is dissolved or dispersed in the medium. The combination of the viscosity-increasing compound and PG compound is excellent in stability and provides long-lasting and increased effects. Viscosity-increasing compound may preferably be selected from the group consisting of acrylate polymers, polyols, cellulose polymers, polysaccharides and polyl-lactams. Examples of the viscosity-increasing compounds include acrylate polymers, or also called as carboxyvinyl polymers, such as carbomer, for example CARBOPOL™ 941, 934, 940, 971, 974, 980 and 981, and polycarbophil, for example NOVEON™ AA-1, CA-1 and CA-2; polyols such as polyvinyl alcohols, glycerin, polyethyleneglycols; cellulose polymers such as methylcellulose, methylethylcellulose, hydroxypropylmethylcellulose, hydroxyethylcellulose, and carboxymethylcellulose; polysaccharides such as carrageenan, gellan gum, xanthan gum, dextran and locust bean gum; polylactams such as polyvinyl pyrrolidone.

Based on the necessity or purpose of the treatment, the viscosity-increasing compound may optionally be a combination of two or more above-described compounds. Further, if it is required, the other viscosity-increasing compounds such as gelatins may be admixed with the above described viscosity-increasing compounds of the present invention.

The amount of the viscosity-increasing compound in the present ophthalmic solution may vary depending on the amount of the PG compound, or the kind or the molecular weight of the viscosity-increasing compound employed. Generally, the amount of about 0.001-30 w/v %, preferably about 0.01-10w/v % of the whole solution is enough to provide the expected effect.

The ophthalmic solution of the present invention may be manufactured by a conventional manner, for example, by adding a PG compound and a viscosity-increasing compound to an aqueous solution such as physiological saline or buffering solution, etc., and dissolving or mixing them or by combining powder composition with the aqueous solution as above or water before use. Further, in order to improve the volubility of the PG compound to water, esters of polyoxyethylene sorbitane mono higher fatty acid such as polysorbate 80, may be added to the purified water. Alternatively, by mixing a PG compound with an ester of polyoxyethylene sorbitane mono higher fatty acid and then adding the mixture to purified water. The concentration of the esters of polyoxyethylene sorbitane mono higher fatty acid may vary depending on the amount of the PG, and in general, may be 0.01-10 w/w %, preferably, 0.05-5 w/w % of whole solution.

In addition, the ophthalmic solution of the present invention may contain other active ingredients in so far as it does not act adverse to the purpose of the present invention.

The ophthalmic solution of the present invention may further contain additives which have been employed in conventional ophthalmic solutions. For example, buffers or isotonic agents such as salts like phosphates (e.g. sodium monohydrogen phosphate and sodium dihydrogen phosphate), borates, sodium chloride or mannitol; dissolving agent such as polysorbate 80 or polyoxyethylene hydrogenated caster oil such as polyethylene hydrogenated caster oil 60; preservatives such as benzalkonium chloride, benzethonium chloride, chloro butanol or paraben.

The present composition may be formulated as a sterile unit dose type product comprising no preservatives.

The ophthalmic solution of the invention is useful for treating glaucoma, cataract or optic nerve disorders, or for lowering the intraocular pressure or for increasing the choroidal blood flow. The ophthalmic solution of the present invention can provide enough therapeutic effect, since it is excellent in stability and the duration and potency of the effect of the PG compound is elongated. Further, the ophthalmic solution of the present invention can provide an improved compliance for the patients due to the reduced administration frequency (e.g. once a day) of the PG compound, which may be expected the reduced side effect such as corneal disorder. Accordingly, the ophthalmic solution of the present invention may be useful for treatment of a various symptoms in the ophthalmic area.

The present invention will be explained in more detail by means of the following examples, which are illustrated by way of example only and never intended to limit the scope of the present invention.

TEST EXAMPLE

Test ophthalmic solutions comprising 0.12 w/v % of 13,14-dihydro-15-keto-20-ethyl-PGF$_2\alpha$ isopropyl ester (test compound 1) were prepared.
Test solution 1: Rescula™ ophthalmic solution (0.12%) (R-tech UENO, Ltd. Tokyo, Japan)
Test solution 2: prepared by adding 1 w/v % methyl cellulose 400 cP to the test solution 1.
Test solution 3: prepared by replacing sodium chloride contained in the test solution 1 as isotonic agent with 3.5 w/v % mannitol and adding 0.3 w/v % gellan gum to the solution.

Normal white rabbits were used. Test solution (30 µL/eye) was administered to one eye and vehicle of the test solution, i.e. the same solution as the test solution except for comprising test compound 1, was administrated to the other eye of the rabbit (30 µL/eye). The intraocular pressure (IOP) of the animals were measured with an applanation tonometer immediately before and 2, 4 and 6 hours after the administration. Change of IOP ($\Delta$IOP) at each measurement time from that measured just before the administration (time 0) was calculated.

Results are shown in tables 1, 2 and 3. Test solution 2 and 3, which comprising certain viscosity-increasing compound, exhibited significantly longer lasting and increased IOP lowering effect than test solution 1 containing no viscosity increasing compound.

TABLE 1

Change of IOP in normal white rabbits after administration of test solution 1

| Test Solution | n | change of IOP (mean ± SE, mmHg) time after administration (hr) | | | |
|---|---|---|---|---|---|
| | | 0 | 2 | 4 | 6 |
| Vehicle for test solution 1 | 8 | 0.0 ± 0.0 | 2.8 ± 0.7 | 1.4 ± 0.9 | 1.1 ± 0.6 |
| Test Solution 1 | 8 | 0.0 ± 0.0 | −2.9 ± 0.7** | −2.0 ± 1.0* | −0.1 ± 1.4 |

**P < 0.01,
*p < 0.05 Compared with the other eye received the vehicle (paired Student's t-test)

TABLE 2

Change of IOP in normal white rabbits after administration of test solution 2

| Test Solution | n | change of IOP (mean ± SE, mmHg) time after administration (hr) | | | |
|---|---|---|---|---|---|
| | | 0 | 2 | 4 | 6 |
| Vehicle for test solution 2 | 8 | 0.0 ± 0.0 | 2.3 ± 0.5 | 2.0 ± 0.7 | 2.0 ± 0.8 |
| Test Solution 2 | 8 | 0.0 ± 0.0 | −3.9 ± 0.7** | −3.3 ± 1.3** | −1.0 ± 1.1* |

**P < 0.01,
*p < 0.05 Compared with the other eye received the vehicle (paired Student's t-test)

TABLE 3

Change of IOP in normal white rabbits after administration of test solution 3

| Test Solution | n | change of IOP (mean ± SE, mmHg) time after administration (hr) | | | |
|---|---|---|---|---|---|
| | | 0 | 2 | 4 | 6 |
| Vehicle for test solution 3 | 8 | 0.0 ± 0.0 | 1.1 ± 1.0 | 0.1 ± 0.8 | 1.3 ± 0.8 |
| Test Solution 3 | 8 | 0.0 ± 0.0 | −3.4 ± 0.5** | −3.6 ± 0.5** | −2.0 ± 1.0** |

**P < 0.01,
*p < 0.05 Compared with the other eye received the vehicle (paired Student's t-test)

Formulation Example 1

Twelve (12) mg of isopropyl unoprostone, 50 mg of CARBOPOL™ 940 and 90 mg of polysorbate 80 were admixed with 50 ml of purified water, more purified water was added to make the total volume 100 ml, and dissolved the mixture to provide Ophthalmic solution 1.

Formulation Example 2

Ophthalmic solution 2 was prepared by the same manner as Example 1 except for 200 mg of polyvinyl alcohol was added in place of CARBOPOL 940.

Formulation Example 3

Ophthalmic solution 3 was prepared by the same manner as Example 1 except for 150 mg of glycerin was added in place of CARBOPOL 940.

Formulation Example 4

Ophthalmic solution 4 was prepared by the same manner as Example 1 except for 20 mg of hydroxymethyl cellulose was added in place of CARBOPOL 940.

Formulation Example 5

Ophthalmic solution 5 was prepared by the same manner as Example 1 except for 100 mg of polyvinyl pyrrolidone was added in place of CARBOPOL 940.

What is claimed is:

1. A method for improving the duration and/or potency of the effect of an ophthalmic solution comprising 13,14-dihydro-15-keto-20-ethyl-prostaglandin F2α isopropyl ester when administered to the eyes of a subject, comprising: adding gellan gum in an amount of about 0.01-10 w/v % to the ophthalmic solution.

2. The method of claim 1, wherein the ophthalmic solution comprises 13,14-dihydro-15-keto-20-ethyl-prostaglandin F2α isopropyl ester in an amount of about 0.001-1 w/v %.

3. The method of claim 2, wherein the ophthalmic solution comprises 13,14-dihydro-15-keto-20-ethyl-prostaglandin F2α isopropyl ester in an amount of about 0.12 w/v %.

4. The method of claim 1, wherein about 0.3-10 w/v % of the gellan gum is added to the solution.

5. The method of claim 4, wherein the ophthalmic solution comprises 13,14-dihydro-15-keto-20-ethyl-prostaglandin F2α isopropyl ester in an amount of about 0.001-1 w/v %.

6. The method of claim 5, wherein the ophthalmic solution comprises 13,14-dihydro-15-keto-20-ethyl-prostaglandin F2α isopropyl ester in an amount of about 0.12 w/v %.

7. The method of claim 1, wherein the method improves the duration of the intraocular pressure lowering effect of the ophthalmic solution to longer than 4 hours.

8. The method of claim 1, wherein the ophthalmic solution is administered to a patient in need thereof only once a day.

9. The method of claim 1, further comprising a dissolving agent.

* * * * *